(12) United States Patent
Bujak

(10) Patent No.: US 9,802,062 B2
(45) Date of Patent: Oct. 31, 2017

(54) METHOD, SYSTEM AND USE FOR THERAPEUTIC ULTRASOUND

(71) Applicant: Matthew Bujak, Toronto (CA)

(72) Inventor: Matthew Bujak, Toronto (CA)

( * ) Notice: Subject to any disclaimer, the term of this patent is extended or adjusted under 35 U.S.C. 154(b) by 0 days.

(21) Appl. No.: 14/390,641

(22) PCT Filed: Mar. 15, 2013

(86) PCT No.: PCT/CA2013/000225
§ 371 (c)(1),
(2) Date: Oct. 3, 2014

(87) PCT Pub. No.: WO2013/149318
PCT Pub. Date: Oct. 10, 2013

(65) Prior Publication Data
US 2015/0100001 A1    Apr. 9, 2015

Related U.S. Application Data

(60) Provisional application No. 61/620,723, filed on Apr. 5, 2012.

(51) Int. Cl.
*A61H 1/00* (2006.01)
*A61N 7/00* (2006.01)
(Continued)

(52) U.S. Cl.
CPC .............. *A61N 7/00* (2013.01); *A61F 9/007* (2013.01); *A61N 7/02* (2013.01); *A61B 2017/00137* (2013.01); *A61B 2090/378* (2016.02); *A61N 2007/0008* (2013.01); *A61N 2007/0039* (2013.01); *A61N 2007/0052* (2013.01)

(58) Field of Classification Search
CPC ............................ A61N 7/00; A61H 23/0245
See application file for complete search history.

(56) References Cited

U.S. PATENT DOCUMENTS 8,025,689 B2    9/2011  Korb et al.
2005/0220820 A1*  10/2005  Sanders et al. ............ 424/239.1
(Continued)

OTHER PUBLICATIONS

Patent Cooperation Treaty, Written Opinion and International Search Report dated Jun. 21, 2013, issued on PCT Application No. PCT/CA2013/000225.
(Continued)

*Primary Examiner* — Tse Chen
*Assistant Examiner* — Hien Nguyen
(74) *Attorney, Agent, or Firm* — Norton Rose Fulbright Canada LLP; Maya Medeiros

(57) ABSTRACT

The described embodiments relate to methods, systems and uses for therapeutic ultrasound, and in particular, to methods, systems and uses for therapeutic ultrasound for treating or alleviating eye conditions. The described embodiments relate to methods, systems and uses that involve an ultrasound device configured for treatment of an eye condition, where the device comprises at least one ultrasound transducer for coupling to at least a portion of an eyelid to supply ultrasound waves to an area proximate to the portion of the eyelid according to treatment parameters, wherein the treatment parameters comprise a treatment frequency and a treatment period.

23 Claims, 7 Drawing Sheets

(51) Int. Cl.
*A61N 7/02* (2006.01)
*A61F 9/007* (2006.01)
A61B 17/00 (2006.01)
A61B 90/00 (2016.01)

(56) References Cited

U.S. PATENT DOCUMENTS

| | | | |
|---|---|---|---|
| 2006/0206173 A1* | 9/2006 | Gertner | A61N 5/0616 |
| | | | 607/88 |
| 2007/0091265 A1* | 4/2007 | Kardon et al. | 351/206 |
| 2008/0081996 A1 | 4/2008 | Grenon et al. | |
| 2008/0097253 A1* | 4/2008 | Pedersen | A61B 8/546 |
| | | | 601/2 |
| 2008/0114420 A1* | 5/2008 | Korb et al. | 607/96 |
| 2008/0154157 A1* | 6/2008 | Altshuler et al. | 601/2 |
| 2011/0319794 A1* | 12/2011 | Gertner | A61N 7/00 |
| | | | 601/3 |
| 2012/0016239 A1* | 1/2012 | Barthe | A61B 8/0858 |
| | | | 600/439 |
| 2014/0221908 A1* | 8/2014 | Sonsino | A61F 9/00772 |
| | | | 604/28 |

OTHER PUBLICATIONS

European Patent Office, Examination Search Report dated Dec. 14, 2015, issued on European Patent Application No. 13772270.8.

\* cited by examiner

METHOD, SYSTEM AND USE FOR THERAPEUTIC ULTRASOUND

FIELD

The described embodiments relate to methods, systems and uses for therapeutic ultrasound, and in particular, to methods, systems and uses for therapeutic ultrasound for treating or alleviating eye conditions.

INTRODUCTION

Eye conditions may relate to meibomian gland dysfunction. Dry eye is a multifactorial disease of epidemic proportions. For example, when extrapolating National Health Services data to the Canadian population, more than 500,000 Canadians may suffer from moderate to severe dry eye. Dry eye can be categorized into two broad categories: aqueous deficient dry eye and evaporative dry eye. Leading experts now speculate that as much as 80% of dry eye may be caused by meibomian gland dysfunction. With blockage of the eyelid meibomian glands and ducts there may be a reduction of lipids within the tear film. This results in instability of the tear film with subsequent early tear break up and evaporation. This ultimately leads to exposure of the corneal surface and a cascade of ocular surface inflammation, thus perpetuating a dysfunctional tear syndrome.

Another example eye condition is a chalazion or meibomian cyst which is a collection of oil or blockage of the meibomian gland and ducts. A further example of an eye condition is a hordeolum or stye which may be an inflamed sebaceous gland of Zeiss. Finally, an additional example is blepharitis which is an inflammation of the eyelid which may predispose subjects to aforementioned eye conditions, such as dry eye, chalazion, hordeolum. Other eye conditions include scarring.

There is a need for improved methods, systems and uses for treating or alleviating eye conditions, such as those associated with the meibomian gland and ducts.

SUMMARY

In a first aspect, embodiments described herein provide a use of an ultrasound device for treatment of an eye condition, wherein the device comprises at least one ultrasound transducer for coupling to at least a portion of an eyelid to supply ultrasound waves to an area proximate to the portion of the eyelid according to treatment parameters.

In some embodiments, the treatment parameters comprise a frequency, an amplitude, on/off cycle, and a treatment period. In some embodiments, the treatment frequency is at least 2 MHz, at least 3 MHz, or between 3 to 5 MHz, or even greater than 5 MHz. In some embodiments, the treatment period is between two to five minutes. These are non-limiting examples. The on/off cycle may be used to pulse the ultrasound waves.

In some embodiments, the device further comprises a controller operable for receiving treatment data, determining the treatment parameters based on the treatment data, and directing the ultrasound transducer according to the treatment parameters.

In some embodiments, the eye condition is caused by dysfunction of the meibomian glands and wherein the area proximate to the portion of the eyelid comprises the meibomian glands and its ductules. In some embodiments, the eye condition is caused by dysfunction of the lacrimal glands and wherein the area proximate to the portion of the eyelid comprises the lacrimal glands and ductules. In some embodiments, the eye condition is caused by dysfunction of the periocular glands and wherein the area proximate to the portion of the eyelid comprises the periocular glands and ductules. In some embodiments, the eye condition is caused by dysfunction of the nasolacrimal system and wherein the area proximate comprises the nasolacrimal system. In some embodiments, the eye condition is caused by dysfunction of the Wolfring glands and wherein the area proximate to the portion of the eyelid comprises the Wolfring glands and ductules. In some embodiments, the eye condition is caused by dysfunction of the Krause glands and wherein the area proximate to the portion of the eyelid comprises the Krause glands and ductules. In some embodiments, the eye condition is caused by dysfunction of the Zeis glands and wherein the area proximate to the portion of the eyelid comprises the Zeis glands and ductules.

In some embodiments, the eye condition is caused by lipids blocked in one or more glands of the eye and wherein the ultrasound waves heat the lipids to emulsify the lipids blocked in the glands and ductules and facilitate flow. In some embodiments, the ultrasound waves heat the lipids to approximately 40 degrees Celsius to increase flow and mobility of the lipids. This is a non-limiting example. In some embodiments, the ultrasound waves supply oscillations to move the emulsified lipids by creating bubbles in the emulsified lipids. In some embodiments, the ultrasound waves supply acoustic streaming to mobilize the emulsified lipids. In some embodiments, the ultrasound waves cause mircocavitation to mobilize the emulsified lipids. In some embodiments, the ultrasound waves stimulate circulation and lymph flow in the area proximate to the portion of the eyelid.

In some embodiments, the ultrasound waves breakdown scar tissue in the area proximate to the portion of the eyelid.

In some embodiments, the ultrasound waves supply continuous ultrasound energy. In some embodiments, the ultrasound waves supply pulsed ultrasound energy defined by on/off cycle.

In some embodiments, the device further comprises a probe for coupling to the ultrasound transducer.

In some embodiments, the device is configured to provide phased array ultrasound to vary ultrasound waves.

In some embodiments, the ultrasound transducer comprises movable components that are configured to move relative to the portion of the eyelid to vary ultrasound waves.

In some embodiments, the device comprises an ultrasound imaging camera and wherein the device is operable in a therapeutic mode to heat the area proximate to the portion of the eyelid and a diagnostic mode to image the area proximate to the portion of the eyelid using the ultrasound imaging camera. In some embodiments, the device can operate in therapeutic mode and diagnostic mode to perform real-time imaging during treatment.

In some embodiments, the ultrasound transducer has a concave shape to complement the eyelid, or the ultrasound transducer has an attachment with a concave shape to complement the eyelid. In some embodiments, the ultrasound transducer has an elliptical shape to complement the eyelid. In some embodiments, the device further comprises an attachment for the ultrasound transducer, wherein the attachment comprises a protective portion for positioning over the eye globe and under the eyelid to protect eye tissue, wherein the protective portion has a concave shape to complement the eyelid.

In some embodiments, the eye condition is selected from the group consisting of dry eye, meibomian gland dysfunction, duct dysfunction, lacrimal gland dysfunction, periocular gland dysfunction, nasolacrimal system dysfunction, post-surgical scarring, and chalazion.

In another aspect, embodiments described herein provide use of an ultrasound device configured for treatment of dry eye, wherein the device comprises at least one ultrasound transducer for coupling to at least a portion of an eyelid to supply ultrasound waves to an area proximate to the lacrimal glands to stimulate aqueous production and flow from the lacrimal glands and ducts.

In another aspect, embodiments described herein provide the use of a high frequency ultrasound device configured for treatment of dry eye, wherein the device comprises at least one ultrasound transducer for coupling to at least a portion of an eyelid to supply ultrasound waves to an area proximate to the meibomian gland to stimulate aqueous production and flow from the meibomian gland and ducts.

In a further aspect, embodiments described herein provide a system for treating an eye condition comprising: an ultrasound device comprising at least one ultrasound transducer for coupling to at least a portion of an eyelid to supply ultrasound waves to an area proximate to the portion of the eyelid according to treatment parameters. In some embodiments, the treatment parameters comprise a frequency, an amplitude, on/off cycle, and a treatment period. Example frequency ranges include at least 2 MHz, at least 3 MHz, and between 3 to 5 MHZ. Greater than 5 MHZ frequencies may also be used to limit depth of penetration into tissue. An example treatment period is between two to five minutes. These are non-limiting examples.

In some embodiments, the system further comprises a controller operable for receiving treatment data from an external source, determining the treatment parameters based on the treatment data, and directing the ultrasound transducer according to the treatment parameters.

In some embodiments, the ultrasound waves heat the area proximate to the portion of the eyelid In some embodiments, the eye condition is caused by lipids blocked in a gland or duct of the eye and wherein the ultrasound waves heat the area proximate to the portion of the eyelid to emulsify the lipids blocked in the gland or the duct and facilitate flow. In some embodiments, the ultrasound waves heat the lipids to approximately 40 degrees Celsius. In some embodiments, the ultrasound waves supply oscillations to move the emulsified lipids by creating bubbles in the emulsified lipids. In some embodiments, the ultrasound waves supply acoustic streaming to mobilize the emulsified lipids. In some embodiments, the ultrasound waves cause mircocavitation to mobilize the emulsified lipids. In some embodiments, the ultrasound waves stimulate circulation and lymph flow in the area proximate to the portion of the eyelid. In some embodiments, the ultrasound waves breakdown scar tissue in the area proximate to the portion of the eyelid. In some embodiments, the ultrasound waves supply continuous ultrasound energy. In some embodiments, the ultrasound waves supply pulsed ultrasound energy.

In some embodiments, the device further comprises a probe for coupling to the ultrasound transducer. In some embodiments, the device is configured to provide phased array ultrasound. In some embodiments, the ultrasound transducer comprises movable components that are configured to move relative to the portion of the eyelid to vary ultrasound waves. In some embodiments, the device comprises an ultrasound imaging camera and wherein the device is operable in a therapeutic mode to heat the area proximate to the portion of the eyelid using the ultrasound waves and a diagnostic mode to image the area proximate to the portion of the eyelid using the ultrasound imaging camera. In some embodiments, the ultrasound transducer has a concave shape to complement the eyelid. In some embodiments, ultrasound transducer has an elliptical shape to complement the eyelid. In some embodiments, the device further comprises an attachment for the ultrasound transducer, wherein the attachment comprises a protective portion for positioning over the eye globe and under the eyelid to protect eye tissue, wherein the protective portion has a concave shape to complement the eyelid. In some embodiments, the eye condition is selected from the group consisting of dry eye, meibomian gland dysfunction, duct dysfunction, lacrimal gland dysfunction, periocular gland dysfunction, nasolacrimal system dysfunction, post-surgical scarring, and chalazion.

In some embodiments, the system may further comprise a roller shaped to complement the eyelid and applied to the eyelid to express the emulsified lipids from the gland or the duct. In some embodiments, the system may further comprise a contact lens to protect ocular tissue around the eye. The lens may be a vaulted scleral contact lens configured for placement over the eye globe and under the eyelid to form a chamber of air between the posterior surface of the contact lens and the cornea. The lens may comprise an absorptive material to block penetration of ocular tissue by the ultrasound waves. In some embodiments, the system may further comprise a lens speculum to elevate the eyelid from the eye globe and create airspace between eye globe and eyelid. In some embodiments, the system may further comprise a temperature measurement mechanism for measuring the temperature of the area proximate to the portion of the eyelid. In some embodiments, the system may further comprise the temperature measurement mechanism comprises a thermal couple. In some embodiments, the system may further comprise a contact lens to protect ocular tissue around the eye, wherein the thermal couple is positioned on the contact lens. In some embodiments, the system may further comprise an ultrasound measurement mechanism for measuring the ultrasounds waves at the area proximate to the portion of the eyelid.

In a further aspect, embodiments described herein provide a method for treating an eye condition using a therapeutic ultrasound device, the method comprising: coupling at least one ultrasound transducer to at least a portion of an eyelid; and propagating ultrasound waves to an area proximate to the portion of the eyelid using the ultrasound transducer according to treatment parameters.

In some embodiments, the treatment parameters comprise a frequency, an amplitude, on/off cycle, and a treatment period. In some embodiments, the method may further comprise placing a contact lens over the eye globe and under the eyelid to protect ocular tissue around the eye. In some embodiments, the lens is a vaulted scleral contact lens configured to form a chamber of air between the posterior surface of the contact lens and the cornea. In some embodiments, the lens comprises an absorptive material to block penetration of ocular tissue by the ultrasound waves. In some embodiments, the method may involve using a lens speculum to elevate the eyelid from the eye globe and create an airspace between eye globe and eyelid. In some embodiments, the eye condition relates to the meibomian glands and wherein the ultrasound waves are supplied for the treatment period to liquefy solidified fats in the meibomian glands. In some embodiments, the eye condition relates to the glands of Zeiss with a hordeolum present and wherein the ultrasound waves are supplied for the treatment period to liquefy fats in the glands of Zeiss when the hordeolum is present.

In some embodiments, the method may further comprise applying ultrasound gel to the surface of the eyelid to act as a coupling medium between eye tissue and the transducer.

In another aspect, embodiments described herein provide use of an ultrasound device configured for treatment of meibomian gland dysfunction caused by solidified fats, wherein the device comprises at least one ultrasound transducer for coupling to at least a portion of an eyelid to supply ultrasound waves to the meibomian glands and ductules to heat the meibomian glands and ductules and liquefy the solidified fats.

In another aspect, embodiments described herein provide use of an ultrasound device configured to promote remodeling and resolution of eyelid scar tissue from the etiology selected from the group consisting of post-surgical, post chalazion, post-inflammatory, and post-infectious, wherein the device comprises at least one ultrasound transducer for coupling to at least a portion of the eyelid to supply ultrasound waves to breakdown scar tissue in the eyelid. This treatment could be combined with topical steroids placed directly on the dermis of the eyelid within the coupling medium. The ultrasound energy could facilitate steroid penetration into the eyelid tissue.

In a further aspect, embodiments described herein provide The use of an ultrasound device configured for treatment of an eye condition, wherein the device is operable in a therapeutic mode and a diagnostic mode, wherein the device comprises at least one ultrasound transducer for coupling to at least a portion of an eyelid to supply ultrasound waves to an area proximate to the portion of the eyelid to diagnose the eye condition in the diagnostic mode and to treat the eye condition according to treatment parameters in the therapeutic mode.

In some embodiments, the ultrasound device is configured to operate in diagnostic mode and therapeutic mode concurrently to provide real-time imaging during treatment.

In another aspect, embodiments described herein provide the use of an ultrasound device configured to facilitate fluid flow down the nasolacrimal system, wherein the device comprises at least one ultrasound transducer for coupling to at least a portion of an inner canthal region of the eye to supply ultrasound waves to an area proximate nasolacrimal system according to treatment parameters.

In another aspect, embodiments described herein provide the use of an ultrasound device configured to break up stones within the nasolacrimal system, wherein the device comprises at least one ultrasound transducer for coupling to at least a portion of an inner canthal region of the eye to supply ultrasound waves to an area proximate nasolacrimal system according to treatment parameters, wherein the treatment parameters comprise a treatment frequency and a treatment period.

DRAWINGS

For a better understanding of embodiments of the systems, methods and uses described herein, and to show more clearly how they may be carried into effect, reference will be made, by way of example, to the accompanying drawings in which.

Figure 1:
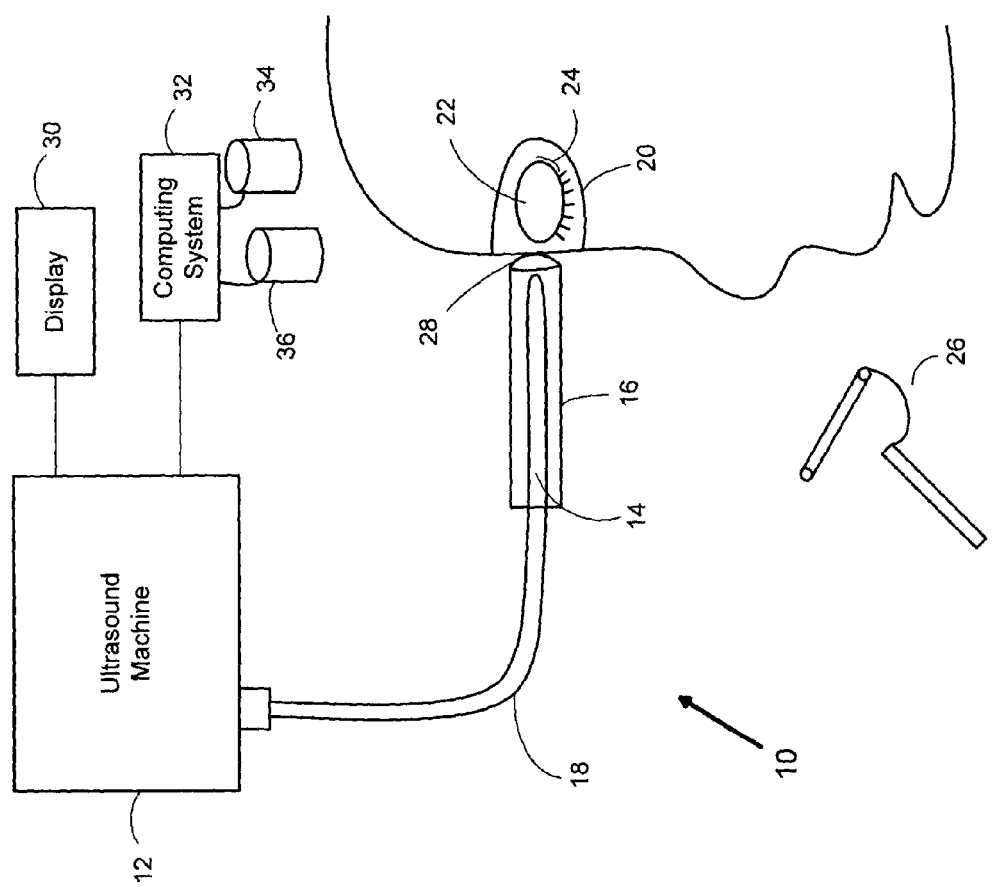
FIG. 1 shows a diagram of a system for eye conditions using therapeutic ultrasound according to some embodiments.

The drawings, described below, are provided for purposes of illustration of the aspects and features of various examples of embodiments described herein. For simplicity and clarity of illustration, elements shown in the figures have not necessarily been drawn to scale. The dimensions of some of the elements may be exaggerated relative to other elements for clarity. Further, where considered appropriate, reference numerals may be repeated among the figures to indicate corresponding or analogous elements.

DESCRIPTION OF VARIOUS EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description should be considered as describing implementation of the various embodiments described herein.

The described embodiments relate to methods, systems and uses for therapeutic ultrasound for treating or alleviating eye conditions, such as dry eye and other conditions associated with gland dysfunction and eyelids.

Eye conditions may relate to meibomian gland dysfunction. For example, one of the underlying causes of dry eye may be meibomian gland dysfunction. Other example eye conditions include chalazion, meibomian cysts, hordeolum, stye, blepharitis and so on. Meibomian gland dysfunction may occur due to a variety of factors. These factors range from keratinization of ductules, inflammation of ducts, solidification of lipid secretions, and atrophy of glands themselves. A meibomian gland blockage, dry eye, and other eye conditions may be ameliorated with heat. The heat required to break up oil secretions involves a treatment that sufficiently warms the eyelid for a period of time. For example, heat treatment may warm the eyelids to 40 degrees Celsius for four minutes. Hot water (wet towel) compresses may be used to apply wet heat to the eyelids. Although efficacious, patient compliance may be a problem and the technique may be error prone as the compress may not warm eyelids to sufficiently warm temperatures. As another treatment approach, a product Lipiflow™ may heat the eyelids and massage them to facilitate expression of oil contents. Although efficacious this treatment product may be costly and a transducer head may have to be purchased for each patient.

The described embodiments relate to methods, systems and uses for therapeutic ultrasound for eye conditions by providing heat and oscillatory ultrasound energy to the eyelids, meibomian glands, lacrimal gland, or other glands and areas proximate eye. By using therapeutic ultrasound energy the depth of tissue penetration may be minimized while the amount of energy delivered to the tissue may be maximized.

For ultrasounds, the frequency used typically ranges from 1 to 3 MHz depending on tissue depth penetration. A 1 MHz ultrasound is typically absorbed at a tissue depth of 3-5 cm. A frequency of 3 MHz is used for superficial lesions at depths of 1-2 cm. Since the eyelid is only several millimeters in thickness a high frequency ultrasound of 2 MHz, 3 MHz or higher may be used by the described embodiments to heat the eyelid and meibomian glands. Alternatively, a normal frequency therapeutic ultrasound may be used at a higher power setting or a longer duration to generate sufficient heat. The use of therapeutic ultrasound may help emulsify blocked fats by two distinct example mechanisms. For example, the high frequency ultrasound may provide heat energy to fats in the gland. The heat energy delivered may liquefy solidified fats. The oscillations would further act to mobilize oil movement through the formation of small bubbles in the oil medium. This may be referred to as microcavitation. Accordingly, the use of therapeutic ultrasound may heat the gland to liquefy fat blockage and create microcavitation. Ultrasound energy may further facilitate movement of oil within the glands and/or ductules through acoustic streaming. The therapeutic ultrasound may also stimulate circulation in the eyelid and meibomian gland, which may promote clearance of inflammatory mediators. Further, the therapeutic ultrasound may help breakdown and remodel scar tissue in the eyelid, which may be the result of a chalazion, or other trauma or infection/inflammation to eyelid. Therapeutic ultrasound may be used post-surgically on the eyelid to reduce scar formation and facilitate healing of tissue after eyelid surgery. These eyelid surgeries could include but would not be limited to blepharoplasty, ptosis repair, entropion repair, ectropion repair, excisional and incisional biopsies and so on. When used to remodel scar tissue therapeutic ultrasound could be combined with other treatments such as intralesional injection of corticosteroids or topical application of steroids and other anti-inflammatories. In this situation therapeutic ultrasound may facilitate penetration of and distribution of medications.

Alternatively, or in conjuction with being directed on the meibomian glands, ultrasound energy could be directed superotemporally in the orbit to focus energy on the lacrimal gland. This acoustic energy may stimulate secretion of tears from the lacrimal gland through to the lacrimal ducts.

In addition to aforementioned applications of therapeutic ocular ultrasound, if the power and frequency settings are varied, ultrasound energy may be directed medially at the nasolacrimal duct apparatus to resolve partial and complete blockages. Ultrasound energy can be used to resolve blockages of the upper and lower canalaculi, the lacrimal sac, or the nasolacrimal duct itself. The ultrasound could be used at lower settings to facilitate flow through the entire apparatus in partial blockages or functional blockages. The ultrasound may be used at higher energy settings to break up stones if they are obstructing the passages. This technique may be directed to stones located anywhere along the entire course of the nasolacrimal system. This ultrasound method may be analogous to the lithotripsy used for treatment of kidney stones. A small probe attachment may be used for this application as it would allow the clinician to focus or broaden ultrasound energy around the desired location.

Referring now to FIG. 1 there is shown a system using therapeutic ultrasound for eye conditions. The system 10 is operable to connect a transducer head 16 to an ultrasound machine 12 via connector 18. The transducer head 16 may be shaped to complement various portions of the eye. Further, the transducer head may include a small probe attachment sized proportional to the portion of the eye to be treated in order to focus or broaden energy on the specific treatment portion of the eye. The transducer head 16 may also include a piezoelectric crystal 14 or numerous crystals as a non-limiting illustrative example. Other example transducer heads 16 are electromagnetic transducers, and so on. In this illustrative example, the system 10 is operable to deliver electricity through the ultrasound machine 12 to the piezoelectric crystals 14 encapsulated in the transducer head 16 coupled to the closed eyelid 24. A gel 20 may be used as a coupling medium to allow direct contact of the transducer head to the closed eyelid 24. The ultrasound machine 12 may operate at a high frequency, such as 2 MHz or higher, for example. A lower frequency at a higher power (or amplitude) may also be used. The delivery of ultrasound energy may be continuous or pulsed. Pulsed energy may allow for a slower heat rise than continuous ultrasound energy at the same intensity. A pulsed ultrasound application may take longer to warm the tissue but may provide a larger safety margin and reduce chance of tissue burn.

The ultrasound machine 12 is configured for treatment of an eye condition, such as dry eye, dysfunction of the meibomian gland, lacrimal gland, periocular gland, and nasolacrimal system, chalazion, and scarring. The ultrasound transducer 16 is adapted for eye treatment and suitable for coupling to at least a portion of an eyelid to supply ultrasound waves to the eyelid according to treatment parameters. The treatment parameters may include a frequency, an amplitude (e.g. power), an on/off cycle (e.g. for pulses), a phase, and a treatment period. An example treatment frequency range is between 1 MHz and 5 MHz, and further examples are provided herein. The treatment parameters may specify a range of frequencies and amplitudes for the ultrasound waves. The ultrasound machine 12 may also be connected to a temperature measurement device (e.g. measurement tool 25 of FIG. 5) that is configured to measure temperature elevations induced by deposition of acoustic energy to the eyelid by the ultrasound transducer 16. If the temperature increases above the range a warning alert may be generated to adjust the treatment parameters or the transducer 16 may be shut down automatically to avoid damage to the eye or eyelid. If the temperature decreases below the range an alert may be generated to adjust the treatment parameters. An example temperature measurement device may be a thermocouple. A measurement device may also measure ultrasound waves and provide the measurement data to ultrasound machine 12. If the ultrasound waves pass a predetermined safety threshold then transducer 16 may automatically shut down or adjust to stay within the safety threshold. An example measurement device for ultrasound waves is a hydrophone.

The frequency range may provide sufficient ultrasound energy to heat the treatment area of the eye. For example, the frequency range of 2 MHz to 5 MHz may provide sufficient ultrasound energy to heat the treatment area of the eye to 40 degrees Celsius. Tissue denaturation may start at temperatures well over 45 when applied for long treatment periods, such as over 100 minutes. The treatment period may be proportional to the treatment frequency, as a lower frequency may require a longer period and vice versa. Example treatment periods range between thirty seconds to twenty minutes, one minute to ten minutes, and two to five minutes. These are non-limiting example treatment periods and others may be used.

The eye condition may be caused by lipids blocked in a gland of the eye and the ultrasound waves may heat the treatment area of the eyelid to emulsify the lipids blocked in the gland. As noted herein, the ultrasound waves may supply oscillations to move the emulsified lipids by creating bubbles in the emulsified lipids, may supply acoustic streaming to mobilize the emulsified lipids, may cause mircocavitation to mobilize the emulsified lipids, stimulate circulation in the area proximate to the portion of the eyelid, and breakdown scar tissue in the area proximate to the portion of the eyelid.

The ultrasound machine 12 may include a controller to receive treatment data from a data source (e.g. computing system 32 or other third party networked system). The controller may process the treatment data to determine the treatment parameters and direct the ultrasound transducer 16 to propagate ultrasound waves according to the treatment parameters. The treatment data may define eye condition, measurements, location, and so on. The ultrasound machine 12 may also connect to an ultrasound imaging camera. The ultrasound machine 12 is operable in a therapeutic mode to heat the area proximate to the portion of the eyelid. The ultrasound machine 12 is operable in a diagnostic mode to image the area proximate to the portion of the eyelid using the ultrasound imaging camera. The diagnostic mode may be used to collect treatment data regarding the eye condition.

The system 10 may also include a roller 26 to express oil secretions from the meibomian glands. The roller 26 may have various shapes, such as a curve or concave shape to complement the eye.

The piezoelectric crystal 14 may be a PZT-8 or similar material, or may use other techniques such as electromagnetic. The ultrasound machine 12 may be powered by various means such as by a standard current or an internal battery. The transducer head 16 may be a plastic material forming a sealed transducer, a head cover, and so on. The transducer head 16 may have various shapes and components, such as a curved or concave shape complementary to eyelid, elliptical shape, a flat head, thin plates extension, probe attachments, and so on. The piezoelectric crystal 14 may contract and expand based on the ultrasonic frequency signals supplied by the ultrasound machine 12 to generate ultrasonic pressure waves which are coupled to the closed eyelid 24 via transducer 16. Any oscillating component with a transducer head 16 may provide ultrasound energy through the probe to the eyelid, meibomian glands, lacrimal gland, periocular glands or nasolacrimal system. The transmission of the pressure waves into the closed eyelid 24 may be enhanced by the gel 20. The ultrasonic pressure waves propagate through the closed eyelid 24 to the meibomian glands, lacrimal gland, periocular glands or nasolacrimal system. Transducer 16 may be held in place by an adhesive, a clip, or by a health assistant for a treatment period. When the treatment is applied by a health assistant the probe may be slowly moved over the closed eyelid 24. Moving the transducer head 16 during treatment may be important because of the following effects: to smooth out irregularities of the near field, to minimize hotspot formation, to reduce irregularities of absorption that might occur due to reflection, interfaces, standing waves, refraction, and differences in tissue thermal conduction or blood flow. It is estimated that at an output 1 W/cm2 there is a rise of 0.8 C/min if vascular cooling effects are ignored.

Alternatively, instead of the transducer head 16 being moved by the clinician over the tissue of the eyelid 24, the transducer head 16 may be stationary or fixed to the eyelid 24. If mobile, a ultrasound transducers could be employed and this may have a single active element that both generates and receives high frequency sound waves, or two paired elements one for transmitting and one for receiving. In contrast, if stationary, a head 16 with multiple components could vary the ultrasound beam applied from the transducer.

The transducer head 16 may have moving components within the head that vary the ultrasound beam applied from the transducer 16.

A phased array may be used to vary the application of the ultrasound across the treatment field. This may allow the clinician to simply apply the transducer 16 (or probe attached thereto) to the eyelid 24 or fasten/adhere it in place without constantly moving the transducer 16 (or probe attached thereto). With this phased array the risk of having a standing wave or a hotspot may be greatly reduced. The phased array could be arranged in a strip (linear array), a ring (annular array), a circular matrix (circular array), or a more complex shape such as an ellipse that would conform to the shape of the eyelids.

Ultrasound energy may be passed into the ocular tissues, which may incite inflammation and potentially cause cataract formation. In accordance with embodiments described herein, systems, methods and uses may involve a vaulted scleral contact lens 22. The lens 22 may be placed over the eye globe and under the eyelids 24 to form a chamber of air between the posterior surface of the contact lens and the cornea itself. Since ultrasound energy does not pass well through gases this vaulted chamber would act as a barrier to ultrasound transmission effectively shielding the eye from the ultrasound energy. Alternatively, a lens speculum may be applied to the eye to elevate eyelid 24 from eye globe and create an airspace between eye globe and eyelid 24.

The system 10 may also include a display for displaying images and video from ultrasound machine 12 and a computing system 32 with a processor and memory 34 for processing captured data, images and video. The computing system 32 and may be operable to store data/images/video in memory 34 and/or an imaging database 36. The transducer 16 may have an imaging component 28. The ultrasound 12 and transducer 16 may be used in a diagnostic setting to image the gland and eyelid 24, as well as a therapeutic setting to heat the eyelid 24 and gland. The gland and surrounding tissues could be imaged in real time as the treatment is provided by the transducer head 16.

Figure 2:
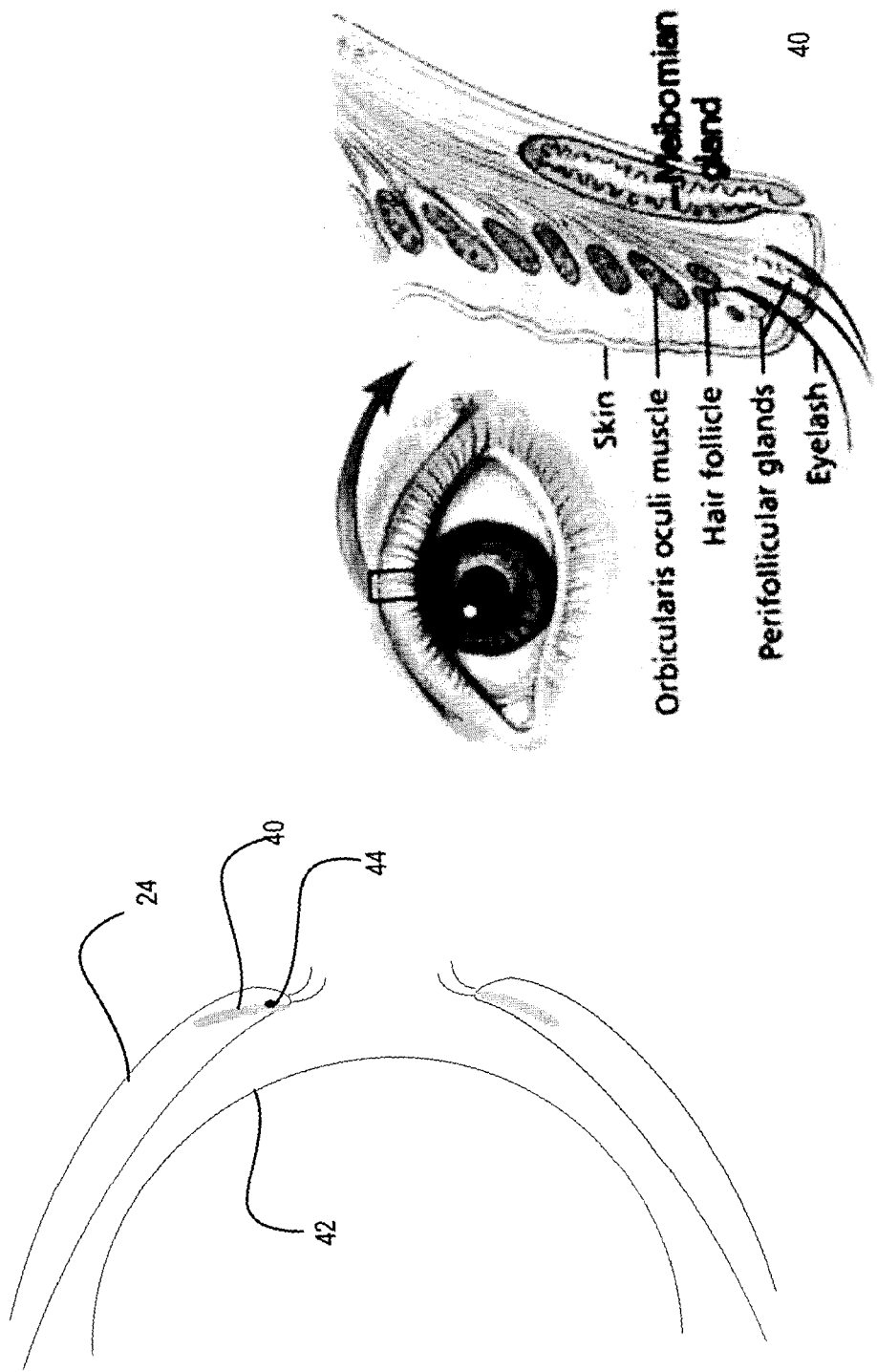
FIG. 2 shows a diagram of a meibomian gland according to some embodiments.

Referring now to FIG. 2 there is shown a diagram of a meibomian gland and duct 40, with a fat blockage 44. There is also shown an illustrative view of the meibomian gland and duct 40. As shown the meibomian gland and duct 40 may be located in the eyelid 24 near the eye globe 42.

Figure 3:
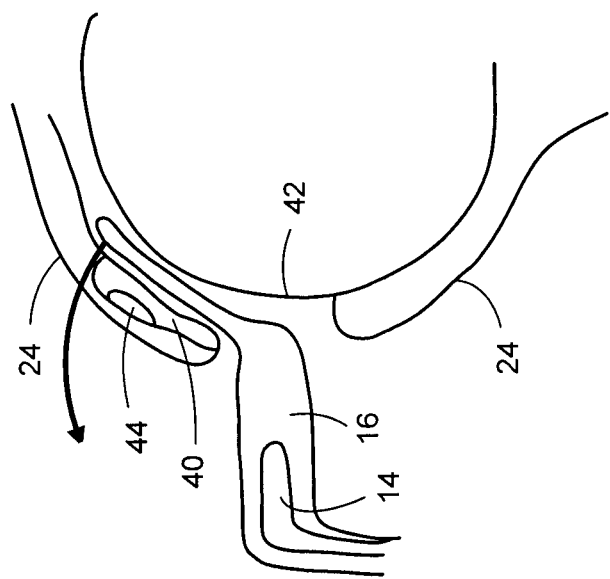
FIG. 3 shows a diagram of a use of therapeutic ultrasound for eye conditions according to some embodiments.
Figure 3:
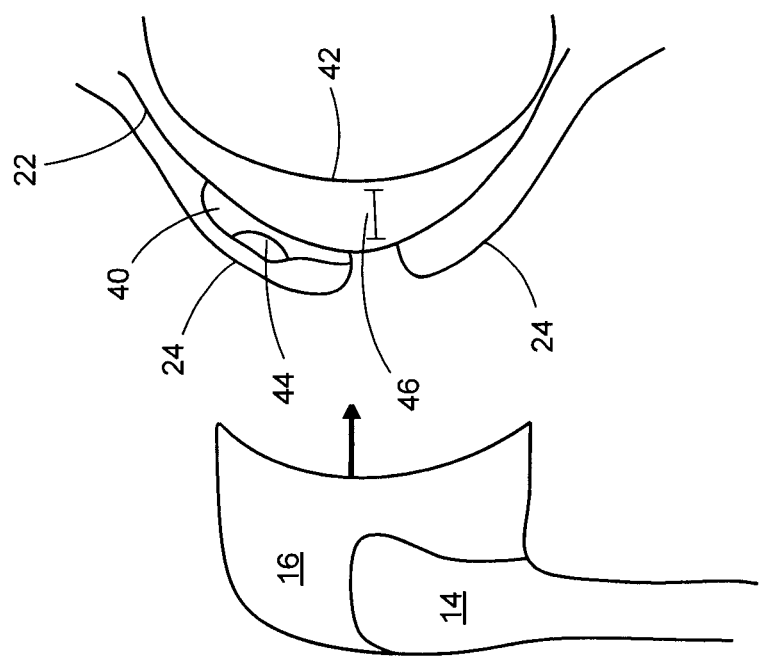

The transducer 16 may be applied to eyelid at different angles and directions. Referring now to FIG. 3 there is shown uses of therapeutic ultrasound for eye conditions. In one example, a transducer head 16 may have a curved shape to complement the eyelid 24. The transducer head 16 may propagate ultrasound waves towards the eyelid 24 and eye globe 42 to liquefy fat blockage 44 in the gland 40. A lens 22 may create a chamber of air 46 to protect eye globe 42. The lens 22 may be placed over the eye globe 42 and under the eyelids 24 to form a chamber of air 46 between the posterior surface of the contact lens 22 and the cornea itself. The contact lens could also be made of an absorptive material that doesn't allow penetration of ultrasound energy. In this case the contact lens would form a sufficient barrier so that it would not need to be vaulted off the globe. Alternatively, a lens speculum (not shown) may be applied to the eye to elevate eyelid 24 from eye globe 42 and create an airspace between eye globe and eyelid 24. In another example, the transducer head 16 may propagate ultrasound waves away from the eye globe 42 using thin plates which form part of transducer head 16.

Figure 5:
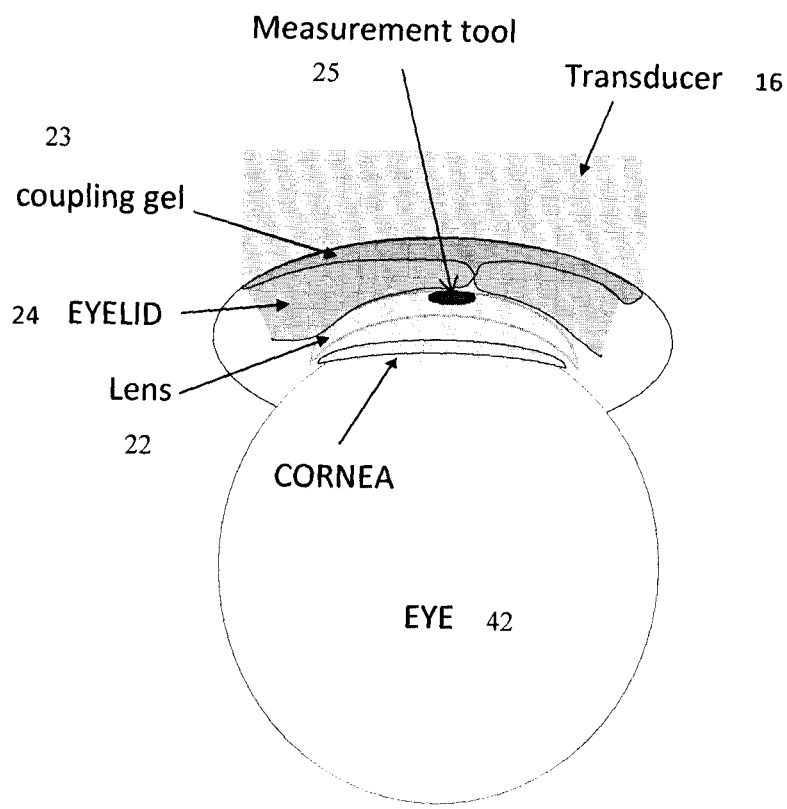
FIG. 5 shows another diagram of a use of therapeutic ultrasound for eye conditions according to some embodiments.

Referring now to FIG. 5 there is shown another diagram of a use of therapeutic ultrasound for eye conditions. The transducer head 16 may have a curved shape to complement the eyelid 24. The transducer head 16 may propagate ultrasound waves towards the eyelid 24 and eye globe 42. A lens 22 may be positioned on top of the cornea and covered by the eyelid 24. The lens 22 may be vaulted to protect eye globe 42 by creating a chamber of air between the posterior surface of the contact lens 22 and the cornea itself. The contact lens could also be made of an absorptive material that doesn't allow penetration of ultrasound energy. In this case the contact lens would form a sufficient barrier so that it would not need to be vaulted off the globe. Coupling gel 23 may be applied on top of the eyelid 24 to act as a coupling medium between the tissue and the transducer 16. Ultrasound waves will be transmitted by the transducer 16 into the eyelid 24. A temperature and attenuation measurement device may be positioned proximate to the lens or other area to collect and record temperatures and attenuation measurements to monitor heating of eye 42. For example, a measurement tool 25 may be positioned on the lens 22 in order to take temperature measurements. The measurement tool 25 may be a thermocouple. The measurement tool 25 may provide temperature data to controller. If the temperature exceeds a safety threshold the controller may automatically shut off the transducer 16 to ensure the eye 42 is not damaged, automatically adjust the treatment parameters to reduce the temperature, or send an alert notification. The measurement tool 25 may be positioned on the lens 22 using glue or other adhesive. It may also be built within the lens 22.

Figure 4:
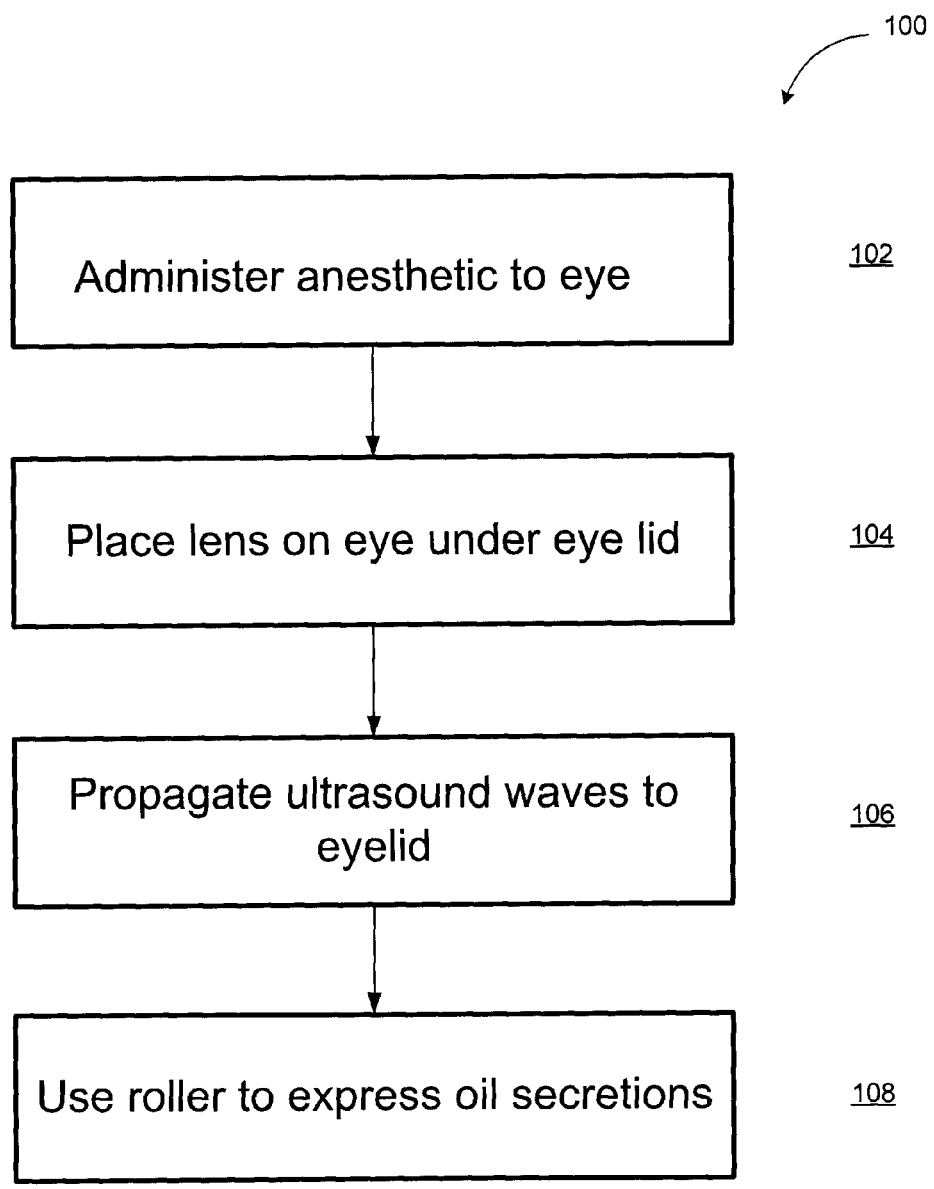
FIG. 4 shows a diagram of a method using ultrasound for eye conditions according to some embodiments.

Referring now to FIG. 4 there is shown a method 100 using high frequency ultrasound for eye conditions. The method 100 may be use high frequency ultrasound to liquefy solidified fats in the meibomian gland, or other glands/ducts. At 102, a clinician may administer a drop of tetracaine or equivalent topical anesthetic unto the eye. At 104, a scleral shield lens 22 may be placed onto the eye. At 106, the ultrasound transducer 16 propagating the high frequency ultrasound waves (such as 3 MHz) may then be applied to both closed eyelids 24 through a coupling gel 20 medium for a treatment period, such as for example a two to five minutes treatment for each eye. After the heating treatment, at 108, a mechanical roller may be used to express oil secretions from the meibomian glands. This may occur while the contact lens shield is still in place. For example, this roller may be applied from a proximal to distal direction in the direction of the meibum flow within the glands themselves. Alternatively, a cotton swap (e.g. Q-tip) or other instrument may be used to guide oil. Post treatment, the patient may be placed on a short course of topical steroids (or NSAIDs) to minimize any post-procedural inflammation.

Figure 6:
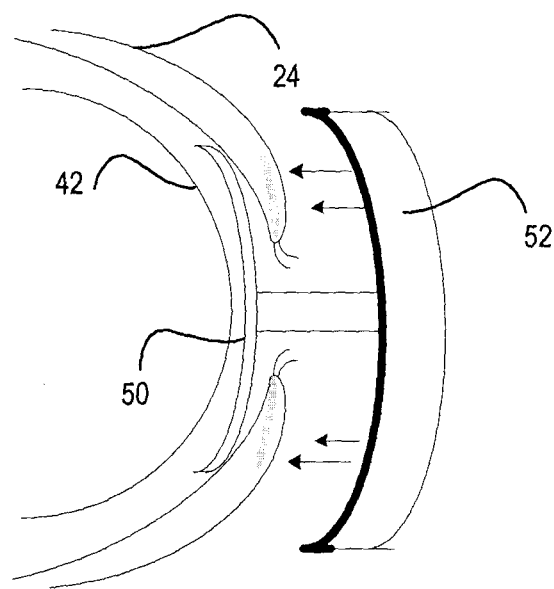
FIG. 6 shows a diagram of a use of therapeutic ultrasound with an attachment for eye conditions according to some embodiments.

Referring now to FIG. 6, there is shown a diagram of a use of therapeutic ultrasound with an attachment for eye conditions according to some embodiments. The attachment 52 may couple to the transducer 16 in order to propagate ultrasound waves to the eyelid 24. The attachment 52 may include a protective portion 50 shaped to complement the eye 42 and protect the eye 42 from the ultrasound waves. The attachment 52 and protective portion 50 may clip onto the patient's head or eye 42 (or otherwise attach) for the duration of the treatment period.

Figure 7:
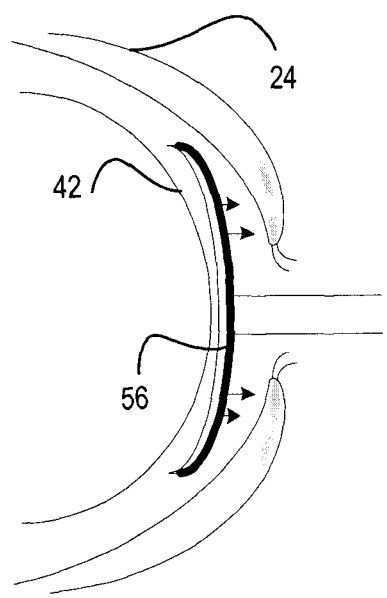
FIG. 7 shows another diagram of a use of therapeutic ultrasound with an attachment for eye conditions according to some embodiments.

Referring now to FIG. 7, there is shown another diagram of a use of therapeutic ultrasound with an attachment for eye conditions according to some embodiments. The attachment 56 may couple to the transducer 16 in order to propagate ultrasound waves through the eyelid 24 but away from eye globe 42. The attachment 56 is shaped to complement the eye 42 and eye lid 24 and position therebetween. In this example, the ultrasound waves propagate away from the eye 42 to reduce chance of harm due to heat. This may protect the eye 42 from the ultrasound waves. The attachment 56 may clip onto the patient's head or eye 42 (or otherwise attach) for the duration of the treatment period.

Embodiments have been described by way of example only, and various modification and variations may be made to these exemplary embodiments.

The invention claimed is:

1. A system for treating an eye condition comprising:
    an ultrasound device comprising at least one ultrasound transducer adapted to couple to at least a portion of an eyelid using a coupling medium to vibrational supply ultrasound waves to an area proximate to the portion of the eyelid according to treatment parameters, the portion of the eyelid including a gland blocked by solidified lipids, the treatment parameters defining a treatment frequency for the ultrasound waves within a frequency range and a treatment period proportional to the treatment frequency;
    a vaulted scleral contact lens to protect ocular tissue, wherein the lens is configured for placement over the eye globe and under the eyelid to form a chamber of air between the posterior surface of the contact lens and the cornea, wherein the chamber of air provides a barrier to the ultrasound waves, the lens being separate from the ultrasound device, wherein the chamber of air provides acoustic impedance so that the ultrasound waves do not propagate the chamber of air;
    a temperature and attenuation measurement device positioned on or within the contact lens to capture measurement data, the measurement data comprising temperature data, the temperature and the attenuation measurement device configured to provide the measurement data to the ultrasound device to compare the temperature data to a predetermined safety threshold, wherein the device generates a warning alert to shut down upon determining if the measurement data is above the predetermined safety threshold or adjust the ultrasound transducer so that the temperature measurement is within the safety threshold upon determining that the temperature data is below the safety range, wherein the temperature measurement device and the attenuation measurement device comprises a thermal couple and a hydrophone;
    an ultrasound imaging camera, wherein the device is operable in a therapeutic mode to heat the area proximate to the portion of the eyelid using the ultrasound waves and a diagnostic mode to image the area proximate to the portion of the eyelid using the ultrasound imaging camera, wherein the ultrasound device is configured to operate in diagnostic mode and therapeutic mode concurrently to provide real-time imaging during treatment;
    wherein the ultrasound waves emulsify the solidified lipids blocking the gland by providing heat energy to the solidified lipids and mobilize the emulsified lipids to promote clearance from the gland using oscillations supplied by the ultrasound waves to create micro cavitation and acoustic streaming of the emulsified lipids.

2. The system of claim 1, wherein the treatment parameters comprise a frequency, an amplitude, on/off cycle, and a treatment period.

3. The system of claim 1, further comprising a controller operable for receiving treatment data from an external source, determining the treatment parameters based on the treatment data, and directing the ultrasound transducer according to the treatment parameters.

4. The system of claim 1, wherein the ultrasound waves heat the area proximate to the portion of the eyelid.

5. The system of claim 1, wherein the eye condition is caused by lipids blocked in a periocular gland or duct and wherein the ultrasound waves heat the area proximate to the portion of the eyelid to emulsify the lipids blocked in the gland or the duct and facilitate flow.

6. The system of claim 1, whereby the ultrasound waves perform at least one of the following:
  stimulating circulation and lymph flow in the area proximate to the portion of the eyelid;
  breaking down scar tissue in the area proximate to the portion of the eyelid;
  causing mirco cavitation to mobilize emulsified lipids blocked in a periocular gland or duct;
  supplying acoustic streaming to mobilize emulsified lips blocked in a periocular gland or duct;
  supplying continuous ultrasound energy; and
  supplying pulsed ultrasound energy.

7. The system of claim 1, wherein the device further comprises a probe for coupling to the ultrasound transducer.

8. The system of claim 1, wherein the device is configured to provide phased array ultrasound to vary the ultrasound waves.

9. The system of claim 1, wherein the ultrasound transducer comprises movable components that are configured to move relative to the portion of the eyelid to vary ultrasound waves.

10. The system of claim 1, wherein the ultrasound transducer has a concave shape or an elliptical shape to complement the eyelid, and wherein the ultrasound transducer is configured to direct ultrasound waves through the eyelid and either away from or towards the eye.

11. The system of claim 1, wherein the device further comprises an attachment for the ultrasound transducer, wherein the attachment comprises a protective portion for positioning over the eye globe and under the eyelid to protect eye tissue, wherein the protective portion has a concave shape to complement the eyelid.

12. The system of claim 1, wherein the lens comprises an absorptive material to block penetration of ocular tissue by the ultrasound waves.

13. The system of claim 1, further comprising a lens speculum to elevate the eyelid from the eye globe and create an airspace between eye globe and eyelid.

14. The system of claim 1, further comprising an ultrasound measurement mechanism for measuring the ultrasounds waves at the area proximate to the portion of the eyelid.

15. A method for treating an eye condition using a therapeutic ultrasound device, the method comprising:
  coupling at least one ultrasound transducer to at least a portion of an eyelid using a coupling medium, wherein the ultrasound device comprises at least one ultrasound transducer for supplying ultrasound waves to an area proximate to the portion of the eyelid according to treatment parameters;
  placing a vaulted scleral contact lens over the eye globe and under the eyelid to protect ocular tissue, the vaulted scleral lens forming a chamber of air between the posterior surface of the contact lens and the cornea, wherein the chamber of air provides a barrier to the ultrasound waves, the lens being separate from the ultrasound device;
  positioning a temperature and attenuation measurement device on or within the contact lens to capture measurement data, the measurement data comprising temperature data, the temperature and attenuation measurement device configured to provide the measurement data to the ultrasound device to compare the temperature data to a predetermined safety threshold, wherein the device generates a warning alert to shut down upon determining if the measurement data is above the predetermined safety threshold or adjust ultrasound transducer so that the temperature measurement is within the safety threshold upon determining that the temperature data is below the safety range, wherein the temperature measurement device and the attenuation measurement device comprises a thermal couple and a hydrophone;
  operating the device in a therapeutic mode to heat the area proximate to the portion of the eyelid by propagating vibrational ultrasound waves to an area proximate to the portion of the eyelid using the ultrasound transducer and the coupling medium according to the treatment parameters, the treatment parameters defining a treatment frequency for the ultrasound waves within a frequency range and a treatment period proportional to the treatment frequency;
  concurrently operating the device in a diagnostic mode to image the area proximate to the portion of the eyelid using the ultrasound imaging camera to provide real-time imaging during treatment;
  providing acoustic impedance using the chamber of air as the ultrasound waves do not propagate the chamber of air;
  emulsifying the solidified lipids blocking the gland using the propagating vibrational ultrasound waves to provide heat energy to the solidified fats; and
  mobilizing the emulsified lipids to promote clearance from the gland using oscillations supplied by the propagating vibrational ultrasound waves that create micro cavitation and acoustic streaming of the liquefied fats.

16. The method claim 15, wherein the treatment parameters comprise a frequency, an amplitude, on/off cycle, and a treatment period.

17. The method of claim 15, wherein the lens comprises an absorptive material to block penetration of ocular tissue by the ultrasound waves.

18. The method of claim 15, further comprising using a lens speculum to elevate the eyelid from the eye globe and create an airspace between eye globe and eyelid.

19. The method of claim 15, wherein the eye condition relates to the meibomian glands and wherein the ultrasound waves are supplied for the treatment period to liquefy solidified fats in the meibomian glands.

20. The method of claim 15, wherein the eye condition relates to the glands of Zeiss with a hordeolum present and wherein the ultrasound waves are supplied for the treatment period to liquefy fats in the glands of Zeiss when the hordeolum is present.

21. The method of claim 15 further comprising applying ultrasound gel to the surface of the eyelid to act as a coupling medium between eye tissue and the ultrasound transducer.

22. The system of claim 1, whereby the ultrasound waves supply oscillations to mobilize the emulsified lipids blocked in a periocular gland or duct by creating bubbles in the emulsified lipids.

23. The method of claim 15 further comprising the ultrasound waves supplying oscillations to mobilize the emulsified lipids blocked in a periocular gland or duct by creating bubbles in the emulsified lipids.

* * * * *